United States Patent [19]

Galindo

[11] 4,219,023
[45] Aug. 26, 1980

[54] CONVEX INSERT AND OSTOMY BAG STRUCTURE

[76] Inventor: Eugene R. Galindo, 2926 Highridge Rd., La Cresenta, Calif. 91214

[21] Appl. No.: 908,746

[22] Filed: May 23, 1978

[51] Int. Cl.³ .............................................. A61F 5/44
[52] U.S. Cl. .................................................. 128/283
[58] Field of Search ................ 128/283, 272, DIG. 24

[56] References Cited

U.S. PATENT DOCUMENTS

| | | | |
|---|---|---|---|
| 2,684,675 | 7/1954 | Perry | 128/283 |
| 2,706,985 | 4/1955 | White | 128/283 |
| 2,928,393 | 3/1960 | Marsan | 128/283 |
| 3,055,368 | 9/1962 | Baxter | 128/283 |
| 3,077,192 | 2/1963 | Berger | 128/283 |
| 3,570,490 | 3/1971 | Berger | 123/283 |
| 4,109,657 | 8/1978 | Carrington | 128/283 |

*Primary Examiner*—Robert W. Michell
*Assistant Examiner*—Thomas Wallen
*Attorney, Agent, or Firm*—Donald M. Cislo

[57] ABSTRACT

An ostomy receptacle or pouch having a convex member insert which is disposed between the flexible pouch or receptacle and the conformable pad or cushion member about the stoma opening so as to obtain relatively snug and close disposition of the ostomy receptacle in relation to the stoma.

9 Claims, 3 Drawing Figures

U.S. Patent    Aug. 26, 1980    4,219,023
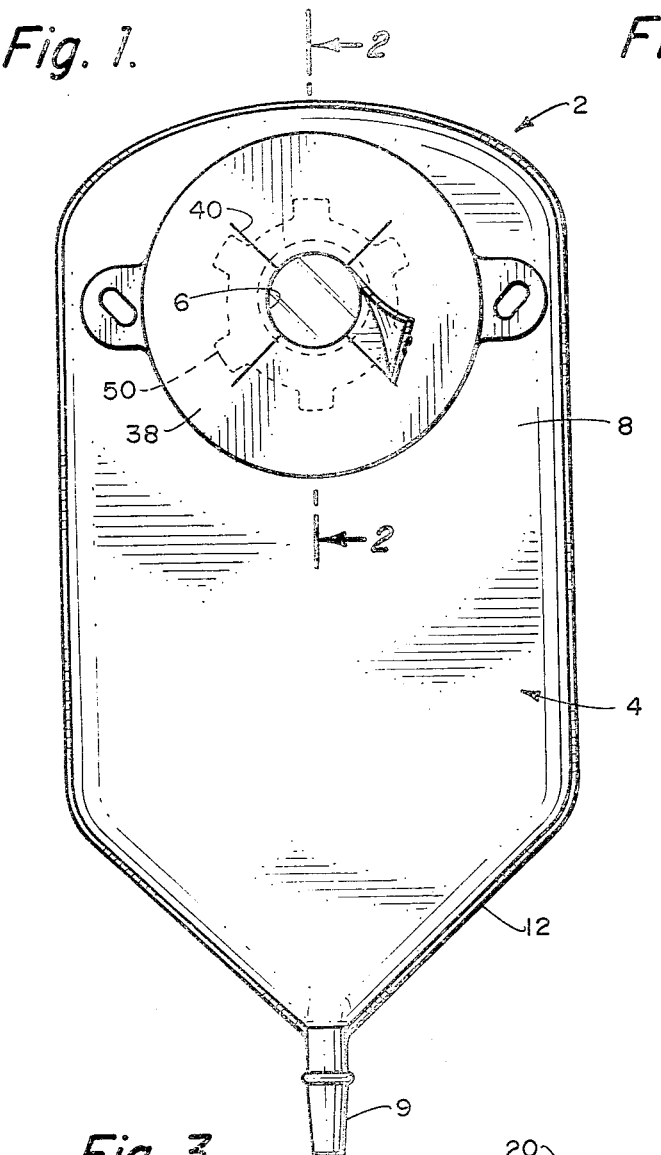
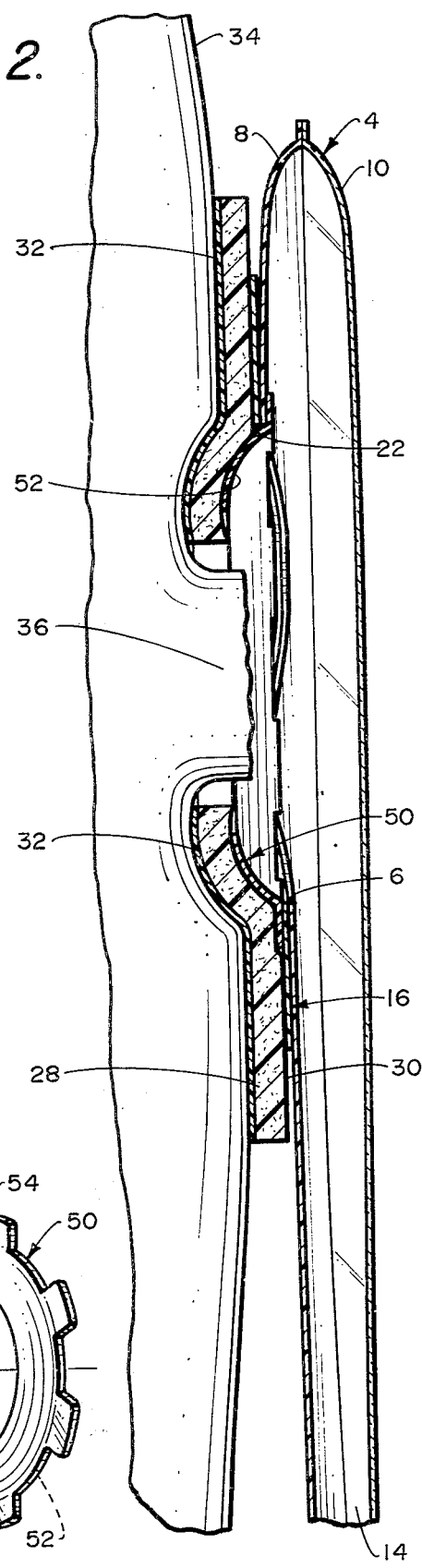
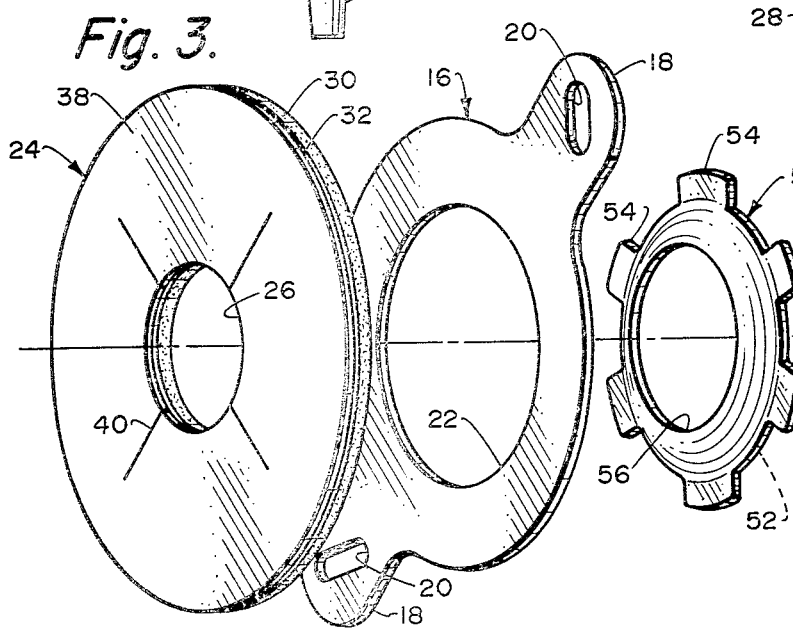

CONVEX INSERT AND OSTOMY BAG STRUCTURE

BACKGROUND OF THE INVENTION

The invention relates to ostomy receptacles and, more particularly, to ostomy structures of the type having a flexible pouch or bag member, with a conformable pad or cushion circumscribing the stoma opening wherein a convex insert is disposed between the bag and conformable pad or circumscribing member so as to outwardly position the ostomy receptacle in snug relationship to the protruding stoma.

The prior art is well aware of various ostomy receptacles and specific constructions thereof, as set forth in U.S. Patents to Berger, U.S. Pat. Nos. 3,077,192 and 3,570,490. The general state of the art is reflected in such prior art patents as Marsan, U.S. Pat. No. 2,928,393, and Baxter, U.S. Pat. No. 3,055,368.

In some of the prior art structures, difficulty has arisen in not having a relatively low-cost, easily manufactured, acceptable ostomy device which fulfills all of the needs and requirements of patients requiring ostomy receptacles.

For example, the prior art is deficient in not having a separate or integral convex insert that may be inserted into the ostomy structure so as to insure snugness of fit around the stoma. That is, in most instances, the flexible pouch or bag making up the ostomy structure is somewhat planar in the area adjacent the stoma, and many times improper fit will cause the waste material to accumulate about the stoma opening of the ostomy receptacle thereby leading to undesirable conditions.

Because of the contours of the human body adjacent a stoma, and the usual planar disposition of the flexible pouch, it is readily apparent that closeness and snugness of fit are generally not attainable, as those of ordinary skill in the art will at once recognize.

With the hereindisclosed invention, a convex insert is provided which has the ability to transform existing prior art ostomy receptacles, of the type employing a flexible pouch having a circumscribing cushion or pad about the ostomy opening, so as to convexively position the ostomy receptacle about the stoma having due regard for the contours of the human body at the stoma site.

The ostomy receptacle of the invention also employs such a convex insert so as to attain closeness of fit of the ostomy receptacle in relationship to the stoma.

It is an object of the invention to provide an ostomy receptacle for proper fit to the body of a wearer in the area adjacent a stoma.

It is a further object of the invention to provide an insert for ostomy receptacles having a flexible pouch and circumscribing, conformable mounting pad so as to obtain closeness of fit, with regard to the stoma, with which the ostomy receptacle is positioned.

It is another further and still more specific object of the invention to provide an ostomy receptacle construction utilizing a flexible bag, having a stoma opening, wherein a mounting pad of conformable nature circumscribes the stoma opening, and wherein a flexible convex insert is interposed the flexible pouch and the mounting pad so as to obtain localized projection of pad and bag, in the area of the stoma, to obtain closeness of fit.

It is still another, even more specific, further object of the invention to provide an ostomy pouch insert member for achieving snug stoma conformity in the ostomy receptacle structure so that emptying of bodily fluids and/or waste into the ostomy receptacle is assured.

It is a further, even more general, specific object of the invention to provide an ostomy structure which is relatively easily manufactured, easily applied and worn, and which attains benefits heretofore not attainable in the prior art.

It is still a further, even more specific, further object of the invention to provide an ostomy receptacle of high attributes which is relatively simple in construction, not requiring complicated and sophisticated manufacturing techniques.

In an exemplary embodiment, the invention is directed to an ostomy pouch insert member for obtaining snug stoma conformity, in a structure having at least a flexible bag, having a stoma opening, with a circumscribing conformable pad thereabout, wherein the insert is an integral, convexively shaped member being annular in configuration and being of thin-wall construction and having a central aperture. The outer, perimetric edge has spaced retaining tabs and the member is of flexible material and is adapted for intermediate disposition between said flexible bag and said circumscribing conformable pad, and is retained in secured relationship by means of said retaining tabs.

In the ostomy receptacle, the structure comprises the combination of a pliable, pouch member having enclosing walls and a stoma receiving opening and a drainage opening. A mounting member having a central opening aligned with said stoma receiving opening is secured to the exterior of said enclosing wall adjacent the stoma opening. A conformable cushion member is secured to the mounting member and has an aligned, corresponding, central opening wherein a flexible convex member, having mounting tabs and an aligned central opening, is disposed intermediate the pliable pouch and the cushion member to urge the area circumscribing the aligned, corresponding, central opening of said cushion member outwardly therefrom, so as to obtain snug fit between the body of the wearer of the ostomy receptacle, about the stoma and the ostomy receptacle itself.

These and further objects of the invention will become apparent from the hereinafter following commentary taken in conjunction with the drawing.

BRIEF DESCRIPTION OF THE DRAWING

FIG. 1 is a side, elevational view of the ostomy receptacle of this invention;

FIG. 2 is an enlarged, fragmented view taken along the line 2—2 of FIG. 1 and showing the ostomy receptacle in position about a stoma and being secured to a portion of the human body;

FIG. 3 is a perspective, fragmented view of the primary components making up the invention, the flexible pouch or bag not being shown.

DESCRIPTION OF THE BEST EMBODIMENTS CONTEMPLATED:

Referring to the figures of the drawing, indicating like elements throughout, it will be noted that the ostomy receptacle 2 of the invention comprises a flexible pouch component 4, having a stoma opening 6 and a lower discharge opening 9. The flexible pouch 4 may be fabricated of thin-walled, heat sealable plastic, and has opposed side walls 8 and 10 and heat sealed along a juncture line 12 thereby forming an interior cavity or chamber 14.

The outwardly exposed wall 10 may be of transparent character so as to easily determine the fluid or waste level in flexible pouch 4. A semi-rigid support or mounting member or shield 16, of annular shape and having opposed ears or tabs 18 with slots 20, is adhered, secured or heat-sealed about the stoma opening 6 and to the wall 8 of pouch 4. It will be noted that the support member 16 has a central aperture 22 of a size at least about as large as the opening 6 in wall 8.

Supported by support or mounting member 16 is annular cushion member 24, in this instance, of rather thin, foam rubber construction adhesively or otherwise secured to the unsealed, exterior surface of member 16, having a central aligned aperture 26 and the surface 28, opposite the surface 30 secured to support member 16, being provided with an adhesive layer 32 for securement to the part of the body 34 in contiguous relationship to stoma 36, as seen in FIG. 2. The annular cushion member 24 is secured to the exterior surface of support or mounting member 16 at a predetermined distance from the periphery of the central aperture 22 of the support or mounting member 16 leaving free an annular area of the exterior surface of the support or mounting member 16 about the perimeter of the central aperture 22.

In the unapplied state, the adhesive layer 32 carries peelable paper cover 38 which acts as a release paper to protect adhesive layer 32. The peelable paper layer 38 may be provided with cuts or perforations 40 to facilitate the insertion of insert member 50 and incidentally the removal of the protective covering.

Disposed between support member 16 and cushion member or pad 24 is convex insert member 50 having an interior, recessed, dish-like portion 52 and spaced retaining tabs 54 for under and over alternate placement between the interior surface of wall 8 and the exterior annular surface of support or mounting member or shield 16 adjacent the periphery of central aperture 22, perimetrically and circumscribing the area about stoma receiving aperture 6, and also contiguous to support or mounting member or shield 16. In the illustration shown, the central opening 22 is coincident with the stoma receiving opening 6 of wall 8.

The convex insert member 50 is of thin-walled, flexible plastic integrally molded so that same may be folded upon itself for insertion in or release from an ostomy structure as shown in FIG. 2, so that the convex portion or opposed surface of interior recessed portion 52 will urge the circumscribing portion of the sponge or mounting pad 24 into close, snug fitting engagement with that portion of the body 34 contiguous and adjacent to stoma 36.

The ostomy receptacle 2 of this invention will generally be made available as shown in FIG. 1 without the convex insert 50 in place. The ostomy receptacle 2 is prepared for use by simply cutting to size, where necessary, the aperture 56 of member 50 before placement in the assemblage as shown in FIG. 2 by means of a scissors or otherwise, and thereafter cutting to size the aperture 26 of cushion pad 24 to receive, in a selectively fitting manner, various sized stomas, as for example 36. In other instances, the wearer will select already precut insert members 50 having selected sized openings or apertures 56 to accommodate that individual's unique needs or requirements. Thereafter, the releasable paper layer 38 is removed and the ostomy receptacle 2 positioned as shown in FIG. 2. If need be, support belts, not shown, may be strung through or connected to the slots 20 of the ears or tab ends 18 of support member 16. Additionally, for wearing use, the ostomy receptacle 2 will have some type of closure or valve means to close off exit 9 of ostomy receptacle 2, not shown.

There has now been described and illustrated an ostomy receptacle insert which will convert existing ostomy structures having at least the flexible pouch and cushion pad in the arrangement shown and discussed, and which will serve to urge the conformable pad or cushion into closer, tight-fitting engagement with the adjacent body surface of the stoma.

Additionally, there is also provided an ostomy receptacle having a unique configuration and structure which is relatively easy to manufacture, not requiring sophisticated components or a multitude thereof, and all of which serve to provide a light-weight, easily used ostomy receptacle having attributes infinitely greater than those in the prior art.

While the invention has been described with respect to specific materials and specific configurations of the elements making up the ostomy receptacle of the invention, those of ordinary skill in the art will at once recognize that certain changes, modifications and alternatives may be made and will readily suggest themselves. All such changes and modifications are intended to be covered by the appended claims and will not detract from the overall essence of the invention as it is embodied in the convex insert or in the ostomy receptacle in which the convex insert is utilized.

I claim:

1. An ostomy receptacle comprising the combination: a pliable pouch member having enclosing walls and a stoma receiving opening and a drainage opening; a mounting member having a central opening aligned with such stoma receiving opening and a surface thereof secured to the exterior of said enclosing wall adjacent the stoma opening; a comfortable cushion member secured a spaced distance from the periphery of said central opening to the opposite surface of said mounting member and having an aligned, corresponding central opening; and a flexible, convex member of thin-walled material and having mounting tabs projecting about the circumference thereof and an aligned central opening and being releasably disposed intermediate said pliable pouch and said cushion member with said mounting tabs extending beyond the periphery of said mounting member alternately on opposite sides of said mounting member to urge the area circumscribing said aligned, corresponding central opening of said cushion member outwardly therefrom.

2. An ostomy receptacle, in accordance with claim 1, wherein said convex member is annular in configuration and has an interior recess, dish-shaped portion and is of molded plastic.

3. An ostomy receptacle, in accordance with claim 2, wherein said mounting member has opposed ears having slots therein adapted to receive support straps.

4. An ostomy receptacle, in accordance with claim 3, wherein said mounting member is of thin ply, semi-rigid plastic and is heat sealably adhered to the exterior wall of said pouch adjacent said stoma receiving opening.

5. An ostomy receptacle, in accordance with claim 4, wherein said cushion member carries an adhesive layer on the surface opposite the surface adhered to said mounting member.

6. An ostomy receptacle, in accordance with claim 5, wherein said adhesive layer on said pad carries a releases-paper covering.

7. An ostomy receptacle, in accordance with claim 6, wherein said convex member has a central aperture which is readily enlargeable in a selective manner.

8. An ostomy receptacle, in accordance with claim 7, wherein said stoma opening, convex member aligned central opening and mounting member opening, and said opening in said cushion member are congruently shaped.

9. An ostomy pouch insert number for obtaining snug stoma conformity in a structure having at least a flexible bag, having a stoma opening with a circumscribing, conformable pad thereabout and a semi-rigid mounting support member intermediate said flexible bag and said pad and having a central opening aligned with said stoma opening, said pad being secured a spaced distance from said central opening of said support member, comprising: an integral, convexly shaped member, being annular in shape and being of thin-walled construction having a central aperture, the outer perimetric edge having spaced retaining tabs, said member being flexible and being adapted for intermediate disposition between said flexible bag and said circumscribing, conformable pad and being retained in secured relationship in a releasable manner by means of said retaining tabs extending beyond the periphery of said central opening of said mounting support member alternately on opposite sides of said mounting support member.

* * * * *